United States Patent
Mowry et al.

(10) Patent No.: US 6,582,463 B1
(45) Date of Patent: Jun. 24, 2003

(54) AUTOANASTOMOSIS

(75) Inventors: David H. Mowry, Eden Prairie, MN (US); John M. Schorgl, Eden Prairie, MN (US)

(73) Assignee: Heartstent Corporation, Brooklyn Park, MN (US)

( * ) Notice: Subject to any disclaimer, the term of this patent is extended or adjusted under 35 U.S.C. 154(b) by 27 days.

(21) Appl. No.: 09/686,689

(22) Filed: Oct. 11, 2000

(51) Int. Cl.[7] .............................................. A61B 17/00
(52) U.S. Cl. ....................................... 623/1.35; 623/1.1
(58) Field of Search ................................ 606/191, 192, 606/194, 195, 198, 151, 153; 128/898, 897; 623/1.1, 1.11, 1.12, 1.13, 1.14, 1.15, 1.16, 1.2, 1.21, 1.23, 1.35, 1.37, 1.17, 900, 903, 920, 922

(56) References Cited

U.S. PATENT DOCUMENTS

| | | |
|---|---|---|
| 5,456,714 A | 10/1995 | Owen |
| 5,944,019 A | 8/1999 | Knudson et al. |
| 5,984,956 A | 11/1999 | Tweden et al. |
| 6,029,672 A | 2/2000 | Vanney et al. |
| 6,096,071 A * | 8/2000 | Yadav ........................ 623/1.15 |
| 6,152,945 A * | 11/2000 | Bachinski et al. .......... 606/198 |
| 6,165,185 A * | 12/2000 | Shennib et al. ............. 606/155 |
| 6,200,339 B1 * | 3/2001 | Leschinsky et al. ........ 623/1.35 |
| 6,251,116 B1 * | 6/2001 | Shennibet et al. .......... 606/155 |
| 6,273,912 B1 * | 8/2001 | Scholz et al. .............. 623/1.31 |
| 6,350,248 B1 * | 2/2002 | Knudson et al. ................ 604/8 |
| 6,361,519 B1 * | 3/2002 | Knudson et al. ................ 604/8 |
| 2001/0014794 A1 | 8/2001 | Moll et al. |

FOREIGN PATENT DOCUMENTS

| | | |
|---|---|---|
| WO | WO 97/31591 | 9/1997 |
| WO | WO 98/08456 | 3/1998 |
| WO | WO 99/36001 | 7/1999 |
| WO | WO 99/38459 | 8/1999 |
| WO | WO 00/21463 | 4/2000 |
| WO | WO 00/41632 | 7/2000 |
| WO | WO 01/17440 A1 | 3/2001 |

* cited by examiner

*Primary Examiner*—Gloria M. Hale
(74) *Attorney, Agent, or Firm*—Merchant & Gould P.C.

(57) ABSTRACT

An attachment member for securing a graft material to a vessel includes a conduit portion for attachment to the graft material. The attachment member has first and second anchor wings formed on opposite sides of an end of the conduit portion. The anchor wings are biased to extend substantially perpendicular to an axis of the conduit portion. The first and second anchor wings have arcuate shapes around substantially collinear axes for the anchor wings to define a flow path within a vessel on opposite sides of the conduit portion.

7 Claims, 6 Drawing Sheets

AUTOANASTOMOSIS

BACKGROUND OF THE INVENTION

1. Field of the Invention

This invention pertains to an attachment member for attaching a graft material to a coronary vessel.

2. Description of the Prior Art

U.S. Pat. No. 5,944,019 issued Aug. 31, 1999 teaches an implant for defining a blood flow conduit directly from a chamber of the heart to a lumen of a coronary vessel. An embodiment disclosed in the aforementioned patent teaches an L-shaped implant in the form of a rigid conduit having one leg sized to be received within a lumen of a coronary artery and a second leg sized to pass through the myocardium and extend into the left ventricle of the heart. As disclosed in the above-referenced patent, the conduit is rigid and remains open for blood flow to pass through the conduit during both systole and diastole. The conduit penetrates into the left ventricle in order to prevent tissue growth and occlusions over an opening of the conduit.

U.S. Pat. No. 5,984,956 issued Nov. 16, 1999 teaches an implant with an enhanced fixation structure. The enhanced fixation structure includes a fabric surrounding at least a portion of the conduit to facilitate tissue growth on the exterior of the implant. U.S. Pat. No. 6,029,672 issued Feb. 29, 2000 teaches procedures and tools for placing a conduit.

Implants such as those shown in the aforementioned patents include a portion to be connected to a coronary vessel and a portion to be placed within the myocardium. Most of the implants disclosed in the above-mentioned patents are rigid structures. Being rigid, the implants are restricted in use. For example, an occluded site may not be positioned on the heart in close proximity to a heart chamber containing oxygenated blood. To access such a site with a rigid, titanium implant, a very long implant must be used. A long implant results in a long pathway in which blood will be in contact with the material of the implant. With non-biological materials, such as titanium, a long residence time of blood against such materials increases the probability of thrombus. The risk can be reduced with anti-thrombotic coatings. Moreover, a rigid implant can be difficult to place while achieving desired alignment of the implant with the vessel. A flexible implant will enhance placement of the implant. U.S. Pat. No. 5,944,019 shows a flexible implant in FIG. 22 of the '019 patent by showing a cylindrical rigid member in the heart wall and a T-shaped rigid member in the coronary artery. The cylindrical and T-shaped rigid members are joined by flexible conduit. Unfortunately, flexible materials tend to be non-biostable and trombogenic and may collapse due to contraction of the heart during systole. PCT/US99/01012 shows a flexible transmyocardial conduit in the form of a cylindrical rigid member in the heart wall and a natural vessel (artery or vein segment) connecting the rigid member to an occluded artery. PCT/US99/00593 (International Publication No. WO99/38459) also shows a flexible conduit. PCT/US97/14801 (International Publication No. WO 98/08456) shows (in FIG. 8c) a transmyocardial stent with a covering of expanded polytetrafluoroethylene.

SUMMARY OF THE INVENTION

According to a preferred embodiment of the present invention, an attachment member is disclosed for securing a graft material to a vessel. The attachment member includes a conduit portion for attachment to said graft material. The attachment member has first and second anchor wings formed on opposite sides of an end of said conduit portion. The anchor wings are biased to extend substantially perpendicular to an axis of the conduit portion. The first and second anchor wings have arcuate shapes around substantially collinear axes for the anchor wings to define a flow path within a vessel on opposite sides of the conduit portion.

DESCRIPTION OF THE PREFERRED EMBODIMENT

Figure 1:
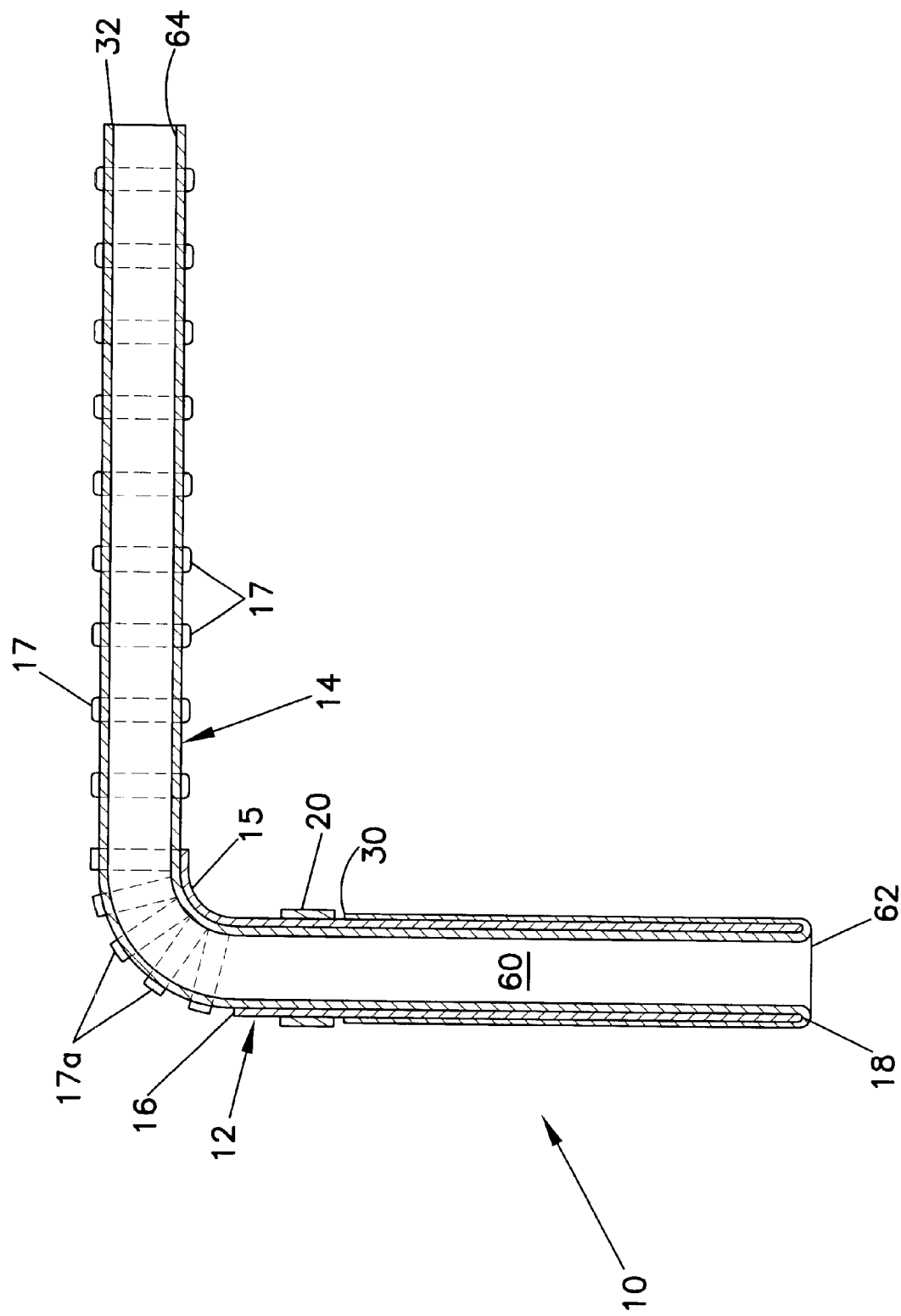
FIG. 1 is a side sectional view of an implant according to the present invention.
Figure 2:
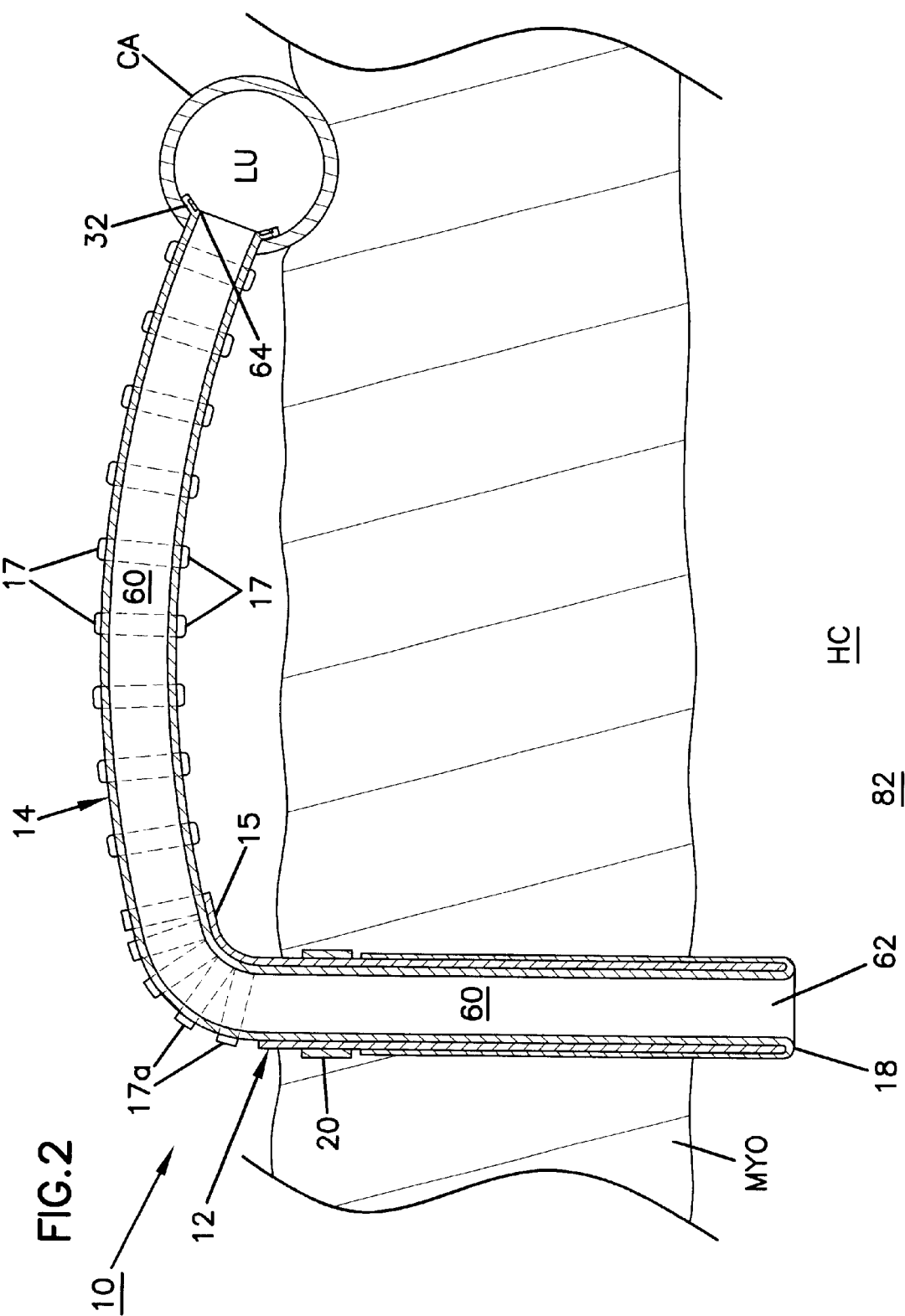
FIG. 2 is a side sectional view of an implant according to the present invention shown in place in a human heart wall with the implant establishing a direct blood flow path from a heart chamber to a coronary vessel.
Figure 3:
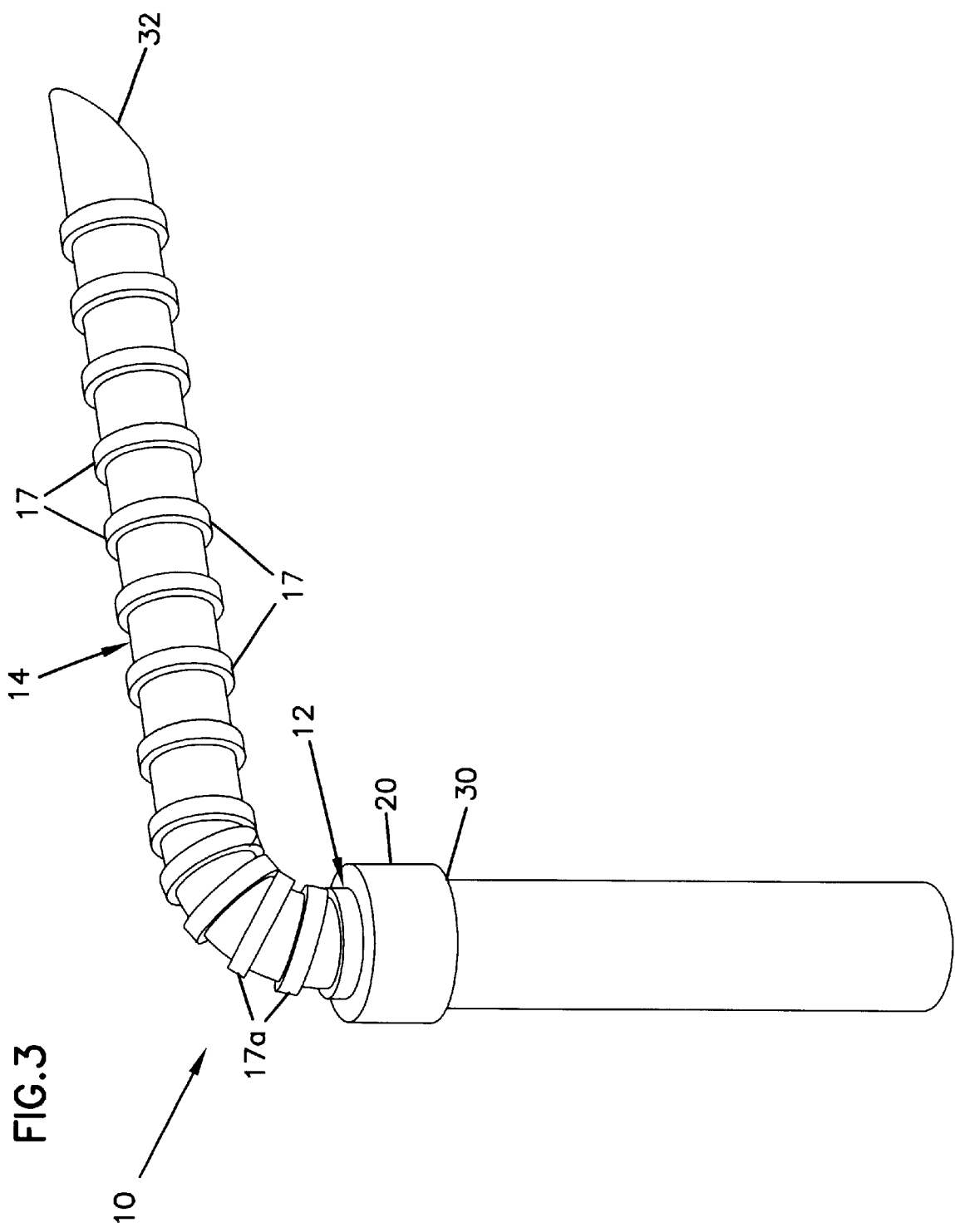
FIG. 3 is a perspective view of the implant of FIG. 1.
Figure 4:
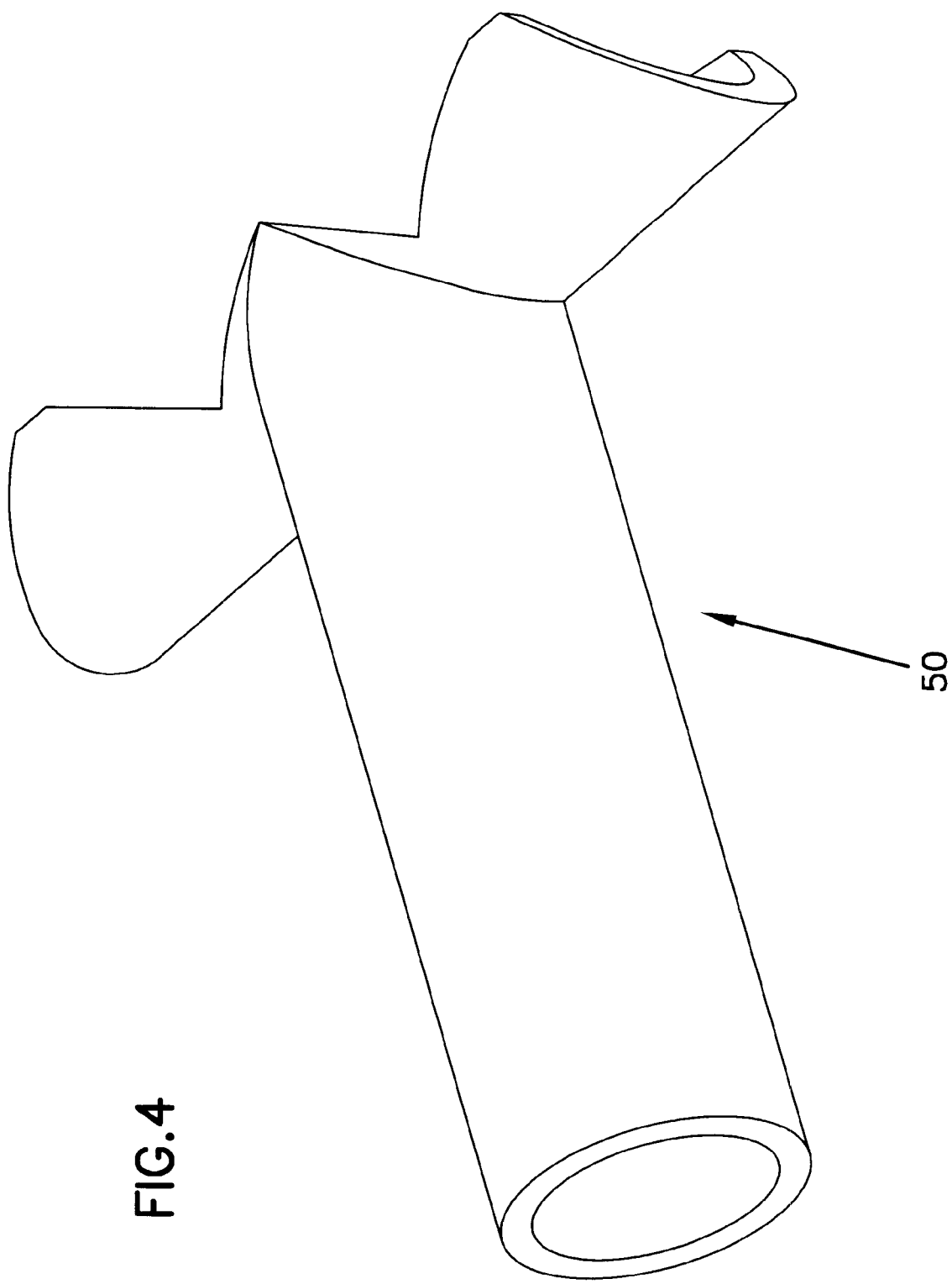
FIG. 4 is a perspective view of a novel attachment member for attachment to a vessel in lieu of a conventional anastomosis.
Figure 5:
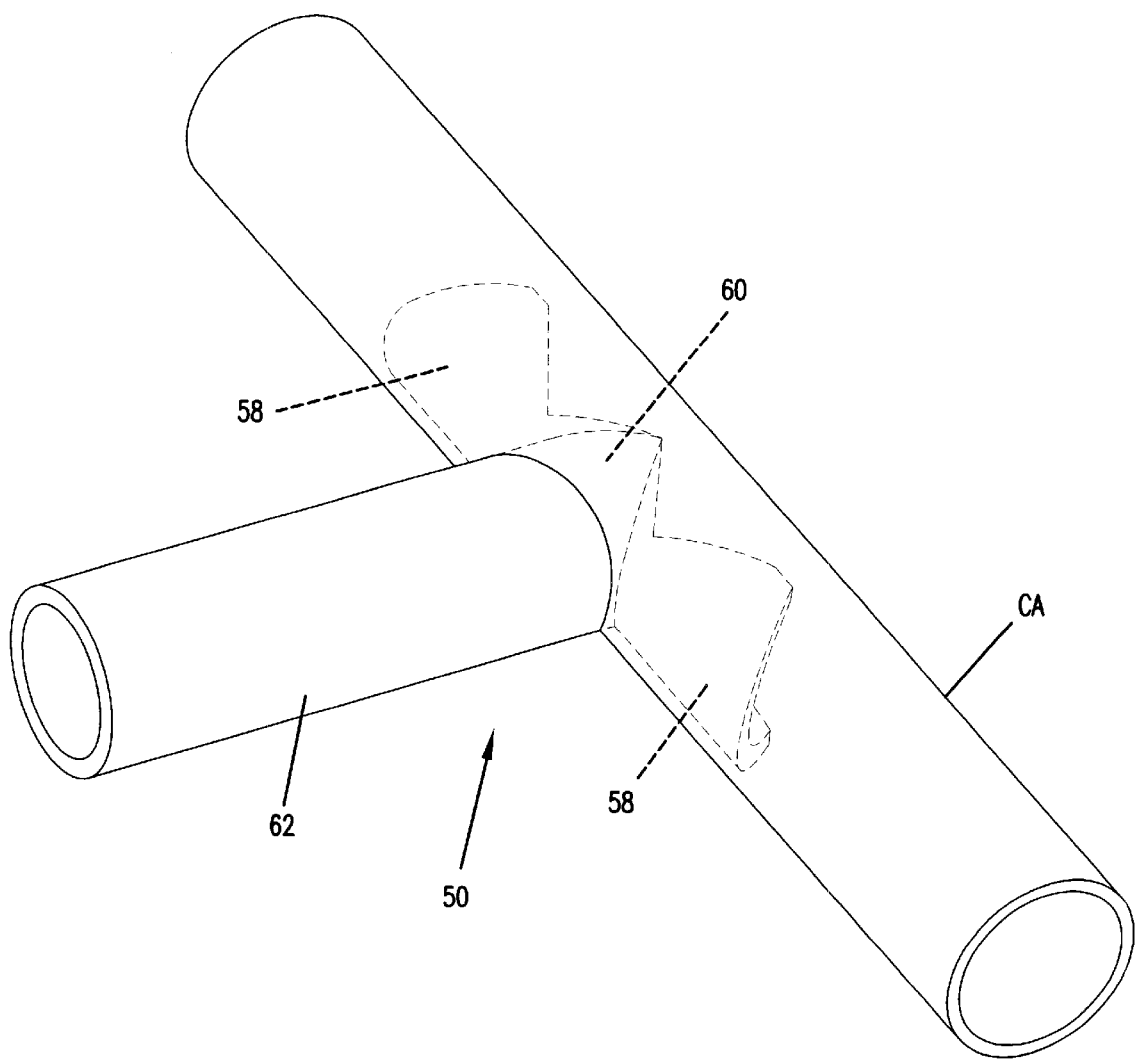
FIG. 5 is the view of FIG. 4 shown attached to a vessel.
Figure 6:
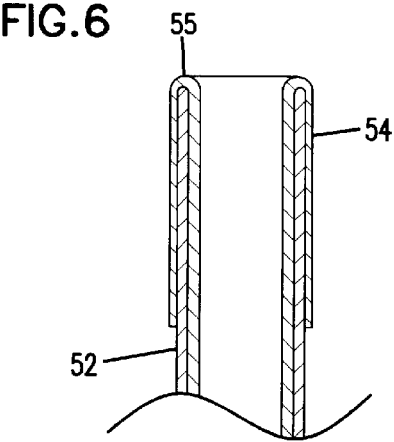
FIG. 6 is a side sectional view of a tube prior to formation of the attachment member of FIG. 4.
Figure 7:
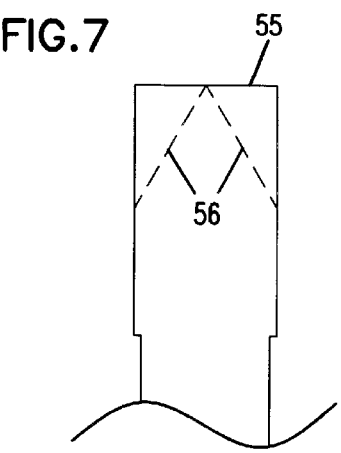
FIG. 7 is a side elevation view of the tube of FIG. 6 with phantom lines indicating a manner of formation of the attachment member of FIG. 4.
Figure 8:
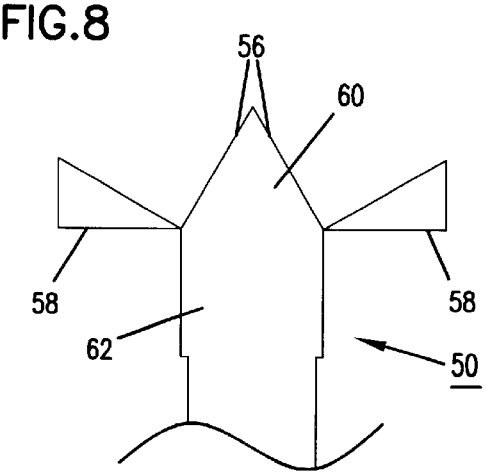
FIG. 8 is a side elevation view of the attachment member following the formation of FIG. 7.
Figure 9:
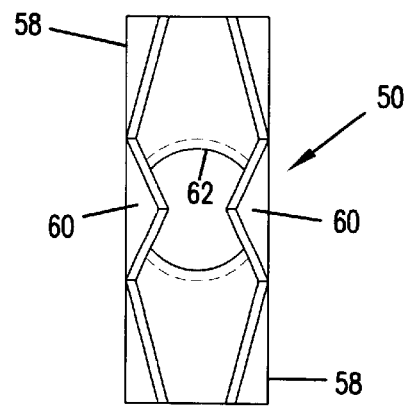
FIG. 9 is a top plan view of the attachment member of FIG. 8.
Figure 10:
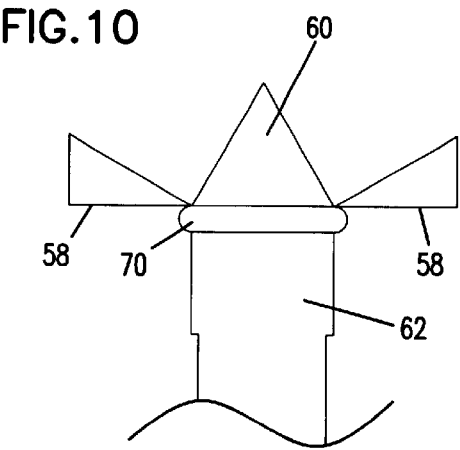
FIG. 10 is the view of FIG. 8 with an optional sewing cuff.
Figure 11:
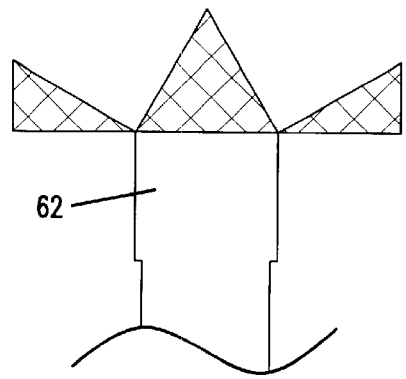
FIG. 11 is the view of FIG. 8 with an alternative embodiment of the attachment member showing an open cell mesh construction in the vessel.

With initial reference to FIGS. 1–3, an implant 10 is shown including a composite of a hollow, rigid cylindrical conduit 12 and a flexible conduit 14. The conduit 12 may be formed of any suitable material. In a preferred embodiment conduit 12 is formed of low density polyethylene ("LDPE"). The material of the conduit 12 is preferably a rigid material in order to withstand contraction forces of the myocardium and hold open a path through the myocardium during both systole and diastole.

The conduit 12 is sized to extend through the myocardium MYO of the human heart to project into the interior of a heart chamber HC (preferably, the left ventricle) by a distance of about 5 mm. The conduit 12 extends from a first (or upper) end 16 to a second (or lower) end 18 (FIG. 1).

As discussed more fully in the afore-mentioned U.S. Pat. No. 5,984,956, the conduit 12 may be provided with tissue-growth inducing material 20 adjacent the upper end 16 to immobilize the conduit 12 within the myocardium MYO. The material 20 surrounds the exterior of the conduit 12 and may be a polyester woven sleeve or sintered metal to define pores into which tissue growth from the myocardium MYO may occur.

The flexible conduit 14 has first and second ends 30, 32 (FIG. 1). The first end 30 of the flexible conduit 14 is inserted through the interior of the conduit 12. The first end 30 is wrapped around the lower end 18 of the conduit 12 such that the first end 30 of the flexible conduit 14 covers the exterior of the conduit 12 adjacent the lower end 18 of the conduit 12. The first end 30 terminates spaced from the upper end 16 of the conduit 12 to expose the tissue-growth inducing material 20.

The first end 30 of the flexible conduit 14 is secured to the rigid conduit 12 by heat bonding along all surfaces of opposing material of the rigid conduit 12 and the flexible conduit 14. At elevated temperatures, the material of the rigid conduit 12 flows into the micro-pores of the material of the flexible conduit 14. The rigid material has a lower melting point than the flexible material.

The rigid conduit 12 and attached flexible conduit 14 are placed in the myocardium MYO with the lower end 18 protruding into the left ventricle HC. The implant 10 thus defines an open blood flow path 60 having a first end 62 in blood flow communication with the left ventricle 82. A second end 64 of the blood flow path 60 communicates directly with the lumen LU of the coronary vessel CA lying at an exterior of the heart wall MYO. To bypass an obstruction in a coronary artery, the end 32 of the flexible conduit 14 is attached to the artery in any suitable manner. For example, the end 32 may be anastomosed to the artery CA with sutures (not shown) in an end-to-side anastomosis as is done in conventional coronary artery bypass procedures. The end 32 is secured to the artery CA distal to the obstruction.

With the above-described embodiment, the implant 10 permits revascularization from the left ventricle HC to a coronary vessel such as a coronary artery CA (or a coronary vein in the event of a retrograde profusion procedure). The use of an elongated, flexible conduit 14 permits revascularization where the vessel CA is not necessarily in overlying relation to the chamber HC. For example, the implant 10 permits direct blood flow between the left ventricle HC and a vessel CA overlying the right ventricle (not shown). The use of a PTFE flexible conduit 14 results in blood flowing through path 60 being exposed only to PTFE which is a material already used as a synthetic vessel with proven blood and tissue compatibility thereby reducing risk of thrombosis and encouraging endotheliazation. As shown in FIG. 1, the flexible conduit 14 is wrapped around the conduit 12 so that no portion of the rigid conduit 12 is in contact with blood within the left ventricle HC.

An interior radius 15 (FIG. 1) is provided on a side of the rigid conduit 12 at end 16. The radius 15 provides support for the flexible conduit 14 and pre-forms the flexible conduit at a preferred 90° bend (a bend of differing degree or no bend could be used).

A plurality of discrete rigid rings 17 are provided along the length of the flexible conduit not otherwise opposing the rigid conduit. Preferably, the rings are LDPE each having an interior surface heat bonded to an exterior surface of the flexible conduit 14. At the radius 15, LDPE rings 17a are integrally formed with the radius 15 with the cross-sectional planes of the rings 17a set at a fixed angle of separation (e.g., about 20 degrees) to support the flexible conduit throughout the 90 degree bend. Again, an interior surface of rings 17a is heat bonded to an exterior surface of the flexible conduit. The rings 17, 17a provide crush resistance. Between the rings 17, 17a, the flexible conduit may flex inwardly and outwardly to better simulate the natural compliance of a natural blood vessel. By way of a further non-limiting example, the discrete rings 17 could be replaced with a continuous helix.

With the foregoing design, an implant of accepted implant material (i.e., LDPE and ePTFE) is formed with blood only exposed to the higher blood compatibility of ePTFE. The constantly open geometry permits a smaller internal diameter of the ePTFE previously attainable with conventional grafts.

FIGS. 4–11 illustrate an invention for attaching a conduit to a vessel in other than a traditional end-to-side anastomosis while permitting blood to flow from the conduit and in opposite directions with a vessel. The embodiment of the invention is illustrated with respect to use with the conduit 10 of FIG. 1 but may be used with any suitable conduit or graft material.

The invention utilizes an attachment member 50 having a generally T-shaped configuration. In a preferred embodiment, the member is formed from a tube 52 of LDPE (FIG. 6) which has interior and exterior lining 54 of ePTFE as described above. In the flexible conduit embodiment described above, the PTFE of the attachment member 50 is an extension of the flexible conduit 14.

The free end 55 of the tube is cut with cuts 56 formed from the center of the free end and angling outwardly to (but not through) the sidewalls of the tube. So cut, two anchor wings 58 are formed on opposite sides of centrally positioned triangular portion 60. The triangular portion 60 is aligned with a cylindrical conduit portion 62. The material can be preformed for the anchor wings 58 to be biased to an outwardly flared position extending perpendicular to the longitudinal axis of the conduit portion 62. The anchor wings 58 and triangular portion 60 are arcuate portions of a cylinder bending around an axis perpendicular to the longitudinal axis of the conduit portion 62.

To attach the member, an incision IN is formed in the artery CA. The free end 55 is placed in the vessel CA and the wings 58 flare outwardly capturing the tube in the artery. A sewing cuff 70 (FIG. 10) may be provided on the tube 62 for stitching to the artery to prevent leakage. Also, a bio-glue may be provided at the incision IN to prevent leaks.

With the embodiment described, ePTFE only is exposed to blood flow. As an alternative, the wings 58 could be formed of open cell mesh material (e.g., nitinol, stainless steel, etc.) (FIG. 11) and left exposed for promoting tissue in-growth similar to that of open cell stents.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims are appended hereto.

What is claimed is:

1. An apparatus for securing a graft material to a vessel, said apparatus comprising:

a conduit portion for attachment to said graft material, said conduit portion having first and second ends;

first and second anchor wings formed on opposite sides of the first end of said conduit portion with said anchor wings biased to extend substantially perpendicular to an axis of said conduit portion;

said first and second anchor wings having arcuate shapes around a substantially collinear axis for said anchor wings to define a flow path within a vessel on opposite sides of said conduit portion;

wherein said second end of the conduit portion is sized to extend through a myocardium of a heart.

2. The apparatus of claim 1, wherein the second end of the conduit portion is sized to extend through the myocardium and project into a heart chamber.

3. An implant for defining a blood flow path from a heart chamber to a coronary vessel, said implant comprising:

a conduit having first and second ends;

said conduit sized to extend through a heart myocardium to place said first end in fluid communication with a heart chamber;

said second end of said conduit adapted for connection to a coronary vessel, said second end including at least two anchor wings moveable between a flared position and a collapsed position, wherein said anchor wings are biased toward the flared position.

4. The implant of claim 3, wherein said conduit is sufficiently rigid to withstand contraction forces of the myocardium and remain open during both systole and diastole.

5. The implant of claim 3, said anchor wings having arcuate shapes around a substantially collinear axis for said anchor wings to define a flow path within a vessel on opposite sides of said conduit portion.

6. The implant of claim 3, wherein said conduit comprises a rigid portion and a flexible portion, the rigid portion being at the first end.

7. The implant of claim 6, further comprising a plurality of discrete rigid rings along a length of the flexible portion.

* * * * *